US006995166B1

(12) United States Patent
Giordano et al.

(10) Patent No.: US 6,995,166 B1
(45) Date of Patent: Feb. 7, 2006

(54) METHOD AND COMPOSITION FOR SUPPLEMENTATION OF NUTRITIONAL DEFICIENCIES IN RENAL PATIENTS

(75) Inventors: John A. Giordano, West Orange, NJ (US); Charles Balzer, Lavalette, NJ (US)

(73) Assignee: Everett Laboratories, Inc., West Orange, NJ (US)

( * ) Notice: Subject to any disclaimer, the term of this patent is extended or adjusted under 35 U.S.C. 154(b) by 0 days.

(21) Appl. No.: 09/671,283

(22) Filed: Sep. 27, 2000

(51) Int. Cl.
A61K 31/51 (2006.01)
A61K 31/44 (2006.01)
A61K 31/355 (2006.01)
A61K 31/34 (2006.01)
A61K 47/00 (2006.01)

(52) U.S. Cl. .............. 514/276; 514/256; 514/458; 514/474; 514/348; 424/439

(58) Field of Classification Search .............. 514/276, 514/251, 458, 474, 348, 256; 424/439
See application file for complete search history.

(56) References Cited

U.S. PATENT DOCUMENTS

| 3,160,564 A | 12/1964 | Hanus ................. 167/81 |
| 4,357,343 A | 11/1982 | Madsen et al. |
| 4,710,387 A | 12/1987 | Uiterwaal et al. ........ 426/72 |
| 4,740,373 A | 4/1988 | Kesselman et al. ...... 424/141 |
| 4,804,535 A | 2/1989 | Kesselman et al. ...... 424/141 |
| 4,940,658 A | 7/1990 | Allen et al. |
| 4,945,083 A | 7/1990 | Jansen, Jr. ............. 514/52 |
| 4,957,938 A | 9/1990 | Anderson et al. |
| 5,093,143 A | 3/1992 | Behr et al. |
| 5,108,767 A | 4/1992 | Mulchandani et al. |
| 5,278,329 A * | 1/1994 | Anderson ............... 556/50 |
| 5,374,560 A | 12/1994 | Allen et al. |
| 5,438,017 A | 8/1995 | Allen et al. |
| 5,457,055 A | 10/1995 | Allen et al. |
| 5,494,678 A | 2/1996 | Paradissis et al. ........ 424/439 |
| 5,514,382 A | 5/1996 | Sultenfuss ............... 424/440 |
| 5,556,644 A | 9/1996 | Chandra ................. 424/630 |
| 5,563,126 A | 10/1996 | Allen et al. |
| 5,626,884 A | 5/1997 | Lockett ................. 424/639 |
| 5,728,678 A | 3/1998 | Trimbo et al. |
| 5,795,873 A | 8/1998 | Allen ..................... 514/52 |
| 5,869,084 A | 2/1999 | Paradissis et al. ........ 424/439 |
| 5,898,036 A * | 4/1999 | McLeod ................. 514/505 |
| 5,922,704 A | 7/1999 | Bland ..................... 514/185 |
| 5,976,568 A * | 11/1999 | Riley |
| 6,042,849 A | 3/2000 | Richardson et al. ....... 424/682 |
| 6,048,846 A | 4/2000 | Cochran |
| 6,054,128 A * | 4/2000 | Wakat .................... 424/195.1 |
| 6,090,414 A | 7/2000 | Passwater et al. ........ 424/702 |
| 6,103,756 A | 8/2000 | Gorsek |
| 6,136,859 A | 10/2000 | Henriksen ............... 514/561 |
| 6,207,651 B1 | 3/2001 | Allen et al. |
| 6,228,388 B1 | 5/2001 | Paradissis et al. ........ 424/439 |
| 6,245,360 B1 | 6/2001 | Markowitz ............... 424/641 |
| 6,255,341 B1 | 7/2001 | DeMichele et al. ....... 514/474 |
| 6,297,224 B1 | 10/2001 | Allen et al. |
| 6,299,896 B1 | 10/2001 | Cooper et al. ........... 424/441 |
| 6,361,800 B1 | 3/2002 | Cooper et al. ........... 424/630 |
| 6,528,496 B1 | 3/2003 | Allen et al. |
| 2001/0028896 A1 | 10/2001 | Byrd ..................... 424/457 |
| 2001/0036500 A1 | 11/2001 | Uchida et al. ........... 426/590 |
| 2002/0015742 A1 | 2/2002 | Jackson et al. .......... 424/630 |
| 2002/0025310 A1 | 2/2002 | Bland .................... 424/94.1 |

FOREIGN PATENT DOCUMENTS

| EP | 0 482 715 | 4/1992 |
| EP | 0 891 719 | 1/1999 |
| WO | 99/07419 | 2/1999 |

OTHER PUBLICATIONS

Centrum, From A to zinc, www.centrum.com/multi/centrum.asp, marketed since 1978.*
GNC Ultra Mega Green, GNC Vitamins and minerals, gnc.mondosearch.com.*
Nephrology Dialysis Transplantation (1998) 13 [Suppl 2]: 23-27.
Holben and Smith, 99(7) Journal of the American Dietetic Assoc. 836-843 (1999).
Pönkä and Kuhlbäck, 213 Acta Med. Scand. 305-307 (1983).
Anderson et al., 54 Am. J. Clin. Nutr. 909-916 (1991).
British Medical Journal, Hypervitaminosis A Accompanying Advanced Chronic Renal Failure (1975).
Burton and Ingold, Vitamin E as an in Vitro and in Vivo Antioxidant 7-22.
Burk, 3 Biological Activity of Selenium 53-70 (1983).
Rolton et al., 6 Nephrol. Dialysis Transplant 440-443 (1991).
Ono, 26(5) Clinical Nephrology 239-243 (1986).
Hultberg et al., 40(4) Clinical Nephrology 230-234 (1993).
Ono, 40 Vitamin E Supplementation in Anemia 440-445 (1985).
Parfrey, 23 Advances in Nephrology 311-330 (1994).
Lacour, 127 Clinica Chimica Acta 205-215 (1983).
Allman et al., 150 The Medical Journal of Australia 130-133.
Vincent, The Biochemistry of Chromium 715-718.
Fraker et al., Link Between Immune Status and Zinc Status 1399S-1406S.

(Continued)

Primary Examiner—Shengjun Wang
(74) Attorney, Agent, or Firm—Preston Gates Ellis & Rouvelas Meeds LLP

(57) ABSTRACT

The present invention relates to compositions and methods for treating the nutritional deficiencies observed in patients suffering from renal disease and associated disorders. Specifically, the method involves administering to a renal patient a composition comprising vitamin C, vitamin E, the B-complex vitamins, chromium, selenium, and zinc.

33 Claims, No Drawings

OTHER PUBLICATIONS

Fukagawa et al., 21 Mineral Electrolyte Metab. 97-100 (1995).
Islam et al., 150 Astherosclerosis 217-224 (2000).
Hoogeveen, Hyperhomocysteinemia, Type 2 Diabetes, and Mortality 1506-1511.
Moustapha, Homocysteine and Renal Failure 138-141.
Robinson et al., 94(11) Circulation 2743-2748 (1996).
Jungers et al., 14 Nephrol. Dialysis Transplant 2903-2906 (1999).
Arnadottir et al., 15 Nephrol. Dialysis Transplant 524-528 (2000).
Janssen et al., 22 Miner Electrolyte Metab. 110-114 (1996).
Bostom et al., 49 Kidney International 147-152 (1996).
Oishi et al., 15 Nephrol. Dialysis Transplant 851-855 (2000).
Perna et al., 25 Mineral and Electrolyte Metabolism 95-99 (1999).
Bogye et al., 84 Nephron 119-123 (2000).
Kornatowska et al., 13 Nephrology Dialysis Transplantation 2829-2832 (1998).
Dierkes et al., 11(2) J. Renal Nutr. 67-72 (2001).
Henning et al., 95(9) Medizin. Klinik 477-81 (2000).
Bazzarre et al., 12(2) J. Amer. Coll. Nutr. 162-69 (1993).
Gey, 52 Bibl. Nutr. Dieta. 75-91 (1995).
Chang et al., 51 Am. J. Clin. Nutr. 826-31 (1990).
Moser-Veillon et al., 52 Am. J. Clin. Nutr. 135-41 (1990).
Kang-Yoon et al., 56 Am. J. Clin. Nutr. 548-58 (1992).
Christian et al., 130(11) J. Nutr. 2675-82 (2000).
Blumberg et al., 20(5) Clin. Nephrol. 244-50 (1983).
Allman et al., 150 Med. J. Australia 130-33 (1999).
Story et al., 27(1) Crit. Care Med. 220-23 (1999).
Makoff, 25 Miner. Electrolyte Metab. 349-51 (1999).
Shah et al., 18(1) Amer. J. Kidney Dis. 84-90 (1991).
Shah et al., 10(1) Amer. J. Kidney Dis. 42-49 (1992).
Vos, 161 Arch. Intern. Med. 774-75 (2001).
House et al., 45(1) ASAIO J. 94-97 (1999).
Descombes et al., 24(10) Artificial Organs 773-78 (2000).
The VITATOPS Trial Study Group, 13 Cerebrovasc. Dis. 120-26 (2002).
Frank et al., 70(4) Int. J. Vitam. Nutr. Res. 159-66 (2000).
Stein et al., 3 Blood Purification 52-62 (1985).

* cited by examiner

METHOD AND COMPOSITION FOR SUPPLEMENTATION OF NUTRITIONAL DEFICIENCIES IN RENAL PATIENTS

FIELD OF THE INVENTION

The present invention relates to compositions comprising various vitamins and minerals, and methods for using these compositions for the treatment of renal disease and associated disorders.

BACKGROUND OF THE INVENTION

The kidney has three major physiological functions: excretory, endocrine, and metabolic. However, regulation and excretion of water, minerals, and other nutrients is the most important function of the kidneys. Metabolic waste products eliminated by the kidneys include urea, creatinine, uric acid, hemoglobin degradation products, and hormone metabolites. The kidneys also play a role in arterial pressure regulation by secreting vasoactive substances such as renin. In addition, the kidneys secrete erythropoietin, which stimulates red blood cell production, and produce 1,25-dihydroxy vitamin $D_3$, the active form of vitamin D. Any of these functions may be impaired in renal disease leading to disruptions in the nutritional status of the patient. TEXTBOOK OF MEDICAL PHYSIOLOGY 315 (Guyton & Hall, $9^{th}$ ed. 1996).

Renal disease is one of the leading causes of morbidity, with millions of individuals affected annually. Generally, renal disease may be classified into two categories: 1) acute renal failure and 2) chronic renal failure. Acute renal failure is characterized by a sudden reduction or cessation of renal function. In contrast, chronic renal failure refers to a progressive loss of renal function, usually a result of an underlying pathological condition. For example, immunological disorders such as lupus erythematosus, metabolic disorders such as diabetes mellitus and hypertension, and infectious diseases such as tuberculosis can lead to chronic renal failure. As renal function continues to deteriorate, patients develop end-stage renal failure (ESRD) that eventually requires dialysis treatment or transplantation. Id., at 413.

Patients with chronic renal failure typically develop generalized edema, acidosis, and uremia, an accumulation of nitrogenous metabolites in the blood. To alleviate these symptoms, patients are placed on dietary therapy or dialysis. The protein-restricted diet prescribed for renal patients is generally deficient in vitamins such as folate, the B vitamins, and vitamin C. HANDBOOK OF NUTRITION AND THE KIDNEY 42 (Mitch & Klahr, eds., $3^{rd}$ ed. 1998) (hereinafter "HANDBOOK"). In addition, the dialysis procedure itself may remove vitamins and nutrient compounds. Gastrointestinal absorption of vitamins may be also altered in patients suffering from chronic renal failure. Makoff, 25 MINER. ELECTROLYTE METABOL. 349–351 (1999).

Compliance with the restrictive renal diet may also result in deficiencies in trace minerals such as zinc and selenium. Highly protein-bound minerals may be lost in excessive amounts in patients with proteinuria. Zima et al., 17 BLOOD PURIF. 182–186 (1999). Furthermore, it has been shown that plasma levels of selenium are decreased in dialysis patients. HANDBOOK, at 43. Poor nutritional status and insufficient levels of vitamins and minerals may place renal patients at higher risk for diseases such as anemia, infections, and cardiovascular disease, or aggravate pre-existing conditions such as hyperlipidemia, osteoporosis, and viral hepatitis. MODERN NUTRITION IN HEALTH AND DISEASE 1447 (Shils et al., eds., $9^{th}$ ed. 1999).

Nutritional intervention is critical to the management of chronic renal disease and end-stage renal disease. Dietary therapy should maintain or improve the nutritional status of the renal patient and minimize or prevent uremic and metabolic toxicities associated with renal failure. The challenge is to simplify a complex dietary regimen while providing an effective nutritional treatment. The nutritional compositions and related methods described herein includes the numerous vitamins and minerals deficient in the restricted diet of the renal patient. Thus, the composition and method of the present invention offers a means to meet the nutritional needs of the renal patient in an uncomplicated approach.

SUMMARY OF THE INVENTION

The present invention provides nutritional compositions and methods of using said compositions for treating patients with renal disease. Specifically, the present invention discloses novel compositions of vitamins and minerals in an amount that can be used to supplement the nutritional deficiencies observed in patients afflicted with renal disease, renal insufficiency, or end-stage renal disease. The compositions of the present invention can also be used as nutritional supplements for patients undergoing dialysis therapy or for patients on a restricted diet. In addition, the compositions can be used to treat the nutritional deficiencies of any disease state that results in increased oxidative stress, elevated cholesterol levels, or elevated homocysteine levels.

The compositions of the present invention comprise numerous vitamins and minerals that will improve the nutritional state of a patient. The vitamins of the present invention preferably comprise vitamin C, vitamin E, vitamin $B_1$, vitamin $B_2$, vitamin $B_3$, vitamin $B_5$, vitamin $B_6$, vitamin $B_{12}$, biotin, and folic acid. The minerals of the present invention preferably comprise chromium, selenium, and zinc.

In a preferred embodiment, the composition comprises about 45 mg to 55 mg vitamin C, 31.5 IU to 38.5 IU vitamin E, 2.7 mg to 3.3 mg thiamine (vitamin $B_1$), 1.8 mg to 2.25 mg riboflavin (vitamin $B_2$), 18 mg to 22 mg niacin (vitamin $B_3$), 9 mg to 11 mg pantothenic acid (vitamin $B_5$), 13.5 mg to 16.5 mg pyridoxine (vitamin $B_6$), 10.8 $\mu$g to 13.2 $\mu$g cyanocobalamin (vitamin $B_{12}$), 270 $\mu$g to 330 $\mu$g biotin, 2.25 mg to 2.75 mg folic acid, 180 $\mu$g to 220 $\mu$g chromium, 63 $\mu$g to 77 $\mu$g selenium, and 18 mg to 22 mg zinc.

In a further preferred embodiment of the present invention, the composition comprises 50 mg of vitamin C, 35 IU vitamin E, 3 mg of thiamine, 2 mg of riboflavin, 20 mg of niacin, 10 mg of pantothenic acid, 15 mg of pyridoxine, 12 $\mu$g cyanocobalamin, 300 $\mu$g of biotin, 2.5 mg of folic acid, 200 $\mu$g of chromium, 70 $\mu$g of selenium, and 20 mg of zinc.

The present invention also relates to methods for supplementing the nutritional deficiencies in a patient comprising the step of administering to said patient a composition comprising vitamin C, vitamin E, B-complex vitamins, chromium, selenium, and zinc. The compositions used in the methods of the present invention may further comprise a pharmaceutically acceptable carrier. In a preferred embodiment, the compositions of the present invention are administered to said patient orally and preferably on a daily basis.

In another embodiment of the compositions of the present invention, vitamin C comprises ascorbic acid, vitamin E comprises d-alpha tocopheryl succinate, pantothenic acid comprises d-calcium pantothenate, niacin comprises niacinamide, selenium comprises L-selenomethionine, zinc comprises L-Optizine ZML-200 InterHealth™, chromium consists of chromium chloride, chromium picolinate, and chromium tripicolinate, and B-complex is one or more vitamins selected from the group consisting of pantothenic acid, cyanocobalamin, niacin, pyridoxine, riboflavin, thiamine, folic acid, and biotin.

DETAILED DESCRIPTION

The nutritional therapy of individuals with renal disease requires a unique formulation due to the multiple metabolic and biochemical changes, as well as dietary restrictions. The prescribed diet restrictions usually result in decreased consumption of vital nutrients such as vitamin C, vitamin E, the B-complex vitamins, and zinc. Rocco et al., 7 J. RENAL NUTR. 17–24 (1997). In addition, patients with end-stage renal disease are often in a uremic state which increases oxidative stress and free radical production, affects the appetite, and alters the body's ability to utilize nutrients. Tetta et al., 17 BLOOD PURIF. 118–126 (1999). The dialysis process may also result in a depletion of essential nutrients. Stein et al., 3 BLOOD PURIF. 52–62 (1985). The novel compositions and related methods of the present invention comprise a unique mixture of vitamins and minerals that are useful as nutritional supplements for treating patients suffering from renal disease.

The term "renal disease" is a generic expression encompassing an array of disorders that afflict the kidneys. The term "renal patient" includes patients suffering from renal disease. In general, renal diseases are categorized according to the affected morphologic component: glomerulus, tubules, and blood vessels. The glomerulus is a network of branching and anastomosing capillaries that filters proteins, toxins, and other substances from the blood. A number of factors may lead to injury to glomeruli including secondary affects from immunologic, vascular, and metabolic diseases. Diseases of the glomerulus include, but are not limited to, glomerulonephritis, nephrotic syndrome, lipoid nephrosis, glomerulosclerosis, Berger disease, and hereditary nephritis. ROBBINS PATHOLOGIC BASIS OF DISEASE 942 (Cotran et al., $6^{th}$ ed. 1999).

The tubules of the kidney reabsorb components from the glomerulus filtrate into the blood. The epithelial cells of the tubules are particularly sensitive to ischemia and toxins and thus, predispose the tubules to injury. Disease conditions of the tubules include, but are not limited to, acute tubular necrosis, tubulointerstitial nephritis, pyelonephritis, urate nephropathy, and nephrocalcinosis. Id., at 968–980.

The richly vascularized kidney receives approximately 25% of the cardiac output and systemic vascular diseases such as vasculitis and hypertension may have secondary effects on renal blood vessels. Other diseases of the renal blood vessels include, but are not limited to, benign nephrosclerosis, renal artery stenosis, thrombotic microangiopathies, hemolytic-uremic syndrome, and sickle cell disease nephropathy. Id., at 981–987. In addition, tumors such as oncocytoma and renal cell carcinoma may also impair renal function. Id., at 991–994. Regardless of the origin, the numerous diseases described above eventually culminate in chronic renal disease and ultimately end-stage renal disease.

Reduced levels of serum vitamin C have been observed in chronic renal failure patients. These reduced levels were most likely due to a low-potassium diet and decreased food intake. Marumo et al., 9 INT. J. ARTIF. ORGANS 17–24 (1986). The low-potassium renal diet generally restricts fruit and vegetables which are abundant in potassium and vitamin C. The major biochemical role of vitamin C is as a cosubstrate in metal catalyzed hydroxylations and it has antioxidant properties interacting directly with superoxide hydroxyl radicals and singlet oxygen. In addition, vitamin C provides antioxidant protection for folate and vitamin E. RECOMMENDED DIETARY ALLOWANCES 115 (National Research Council, $10^{th}$ ed., 1989) (hereinafter "RDA"). One embodiment of the compositions of the present invention provides a supplemental dose of vitamin C, preferably in the amount of about 45 to about 55 mg.

Vitamin E is an antioxidant found in biological membranes where it protects the phospholipid membrane from oxidative stress. RDA, at 99–101. It is also an antiatherogenic agent and studies have demonstrated a reduced risk of coronary heart disease with increased intake of vitamin E. Stampfer et al., 328 N. ENGL. J. MED. 1444–1449 (1993). Decreased levels of vitamin E have been observed in chronic renal failure patients and in patients undergoing dialysis. Taccone-Gallucci et al., 27 CLIN. NEPHROL. 238–241 (1987); Ito et al., 217 JAMA 699 (1971). In addition, it has been demonstrated that the typical renal diet is deficient in vitamin E. Ono, 40 NEPHRON 440–445 (1985). Furthermore, atherosclerotic cardiovascular disease is a leading cause of death in patients with end-stage renal disease. Maiorca, et al., 43 KIDNEY INT. S4–S10 (1993). Thus, one embodiment of the compositions of the present invention provides a supplemental dose of vitamin E, preferably in the amount of about 31.5 to about 38.5 IU.

Thiamine (vitamin $B_1$) is a coenzyme for the oxidative decarboxylation of α-ketoacids and for transketolase which is a component of the pentose phosphate pathway. The activity of thiamine is inhibited by folate deficiency and malnutrition. RDA, at 123. Chronic renal failure patients placed on a low protein diet exhibited a thiamine deficiency. Porrini et al., 59 INT. J. VITAM. NUTR. RES. 304–308 (1989). In addition, erythrocyte transketolase activity was impaired in dialysis patients. Descombes et al., 43 KIDNEY INT. 1319–1328 (1993). Hence, to correct for any potential thiamine deficiency in renal patients, one embodiment of the compositions of the present invention may also comprise thiamine, preferably in the amount ranging from about 2.7 to about 3.3 mg.

Riboflavin (vitamin $B_2$) is a component of two flavin coenzymes, flavin mononucleotide (FMN) and flavin adenine dinucleotide (FAD). These flavoenzymes are involved in a number of oxidation-reduction reactions including the conversion of pyridoxine and niacin. RDA, at 132. Renal patients prescribed a low protein diet demonstrated evidence of riboflavin deficiency. Porrini et al., 59 INT. J. VITAM. NUTR. RES. 304–308 (1989); Stein et al., 3 BLOOD PURIF. 52–62 (1985). Corneal vascularization and dermatitis has been noted in patients exhibiting riboflavin deficiency. HANDBOOK, at 116. Thus, one embodiment of the compositions of the present invention may comprise riboflavin, preferably in the amount ranging from about 1.8 to about 2.2 mg.

Nicotinamide adenine dinucleotide (NAD) and NAD phosphate (NADP) are active coenzymes of niacin (vitamin $B_3$). These coenzymes are involved in numerous enzymatic reactions such as glycolysis, fatty acid metabolism, and steroid synthesis. Niacin is also required for the synthesis of pyroxidine, riboflavin, and folic acid. RDA, at 137. Administration of niacin may also produce a reduction in total cholesterol, LDL, and VLDL levels and an increase in HDL cholesterol. Henkin et al., 91 AM. J. MED. 239–246 (1991). A niacin deficiency was noted in dialysis patients and reduced amounts of niacin have been demonstrated in a low protein renal diet. DeBari et al., 39 AM. J. CLIN. NUTR. 410–415 (1984); Mackenzie et al., 5 PROC. EUR. DIAL. TRANSPLANT. ASSOC. 172–178 (1968). Thus, to maintain appropriate niacin levels in renal patients, one embodiment of the compositions of the present invention may comprise niacin, preferably in the amount ranging from about 18 to about 22 mg.

Pantothenic acid (vitamin $B_5$) is a component of the coenzyme A macromolecule which is required for the synthesis of fatty acids, cholesterol, steroid hormones, and neurotransmitters. The coenzyme A complex also has a major role in the acetylation and acylation of numerous proteins. RDA, at 169. Low protein diets as typically prescribed for renal patients provide a minimum amount of pantothenic acid. In addition, a decrease in pantothenic acid plasma levels was observed in dialysis patients. Mackenzie et al. 5 PROC. EUR. DIAL. TRANSPLANT. ASSOC. 172–178 (1968). Therefore, to minimize a deficiency of pantothenic acid in renal patients, one embodiment of the compositions of the present invention may comprise pantothenic acid, preferably in the amount ranging from about 9 to about 11 mg.

The active forms of pyridoxine (vitamin $B_6$), pyridoxal-5'-phosphate (PLP) and pyridoxamine-5'-phosphate, are coenzymes for numerous enzymes and as such, are essential for gluconeogenesis, niacin formation, and erythrocyte metabolism. RDA at, 142–143. A high incidence of pyridoxine deficiency has been noted in both adult and pediatric chronic renal failure patients, as well as patients undergoing dialysis. Stein et al., 3 BLOOD PURIF. 52–62 (1985); Stockberger et al., 7 NUTR. RES. 1021–1030 (1987); Descombes et al., 43 KIDNEY INT. 1319–1328 (1993). Low protein diets generally have minimal amounts of pyridoxine. Kopple et al., 19 KIDNEY INT. 694–704 (1981). A deficiency in pyridoxine may be attributed to the suppressed immune function observed in chronic renal patients, as well as the increased plasma and tissue oxalate concentrations in renal failure. Dobblestein et al., 5 KIDNEY INT. 233–239 (1974); Morgan et al., 46 NEPHRON 253–257 (1987).

In addition, it has been suggested that pyridoxine deficiency plays a role in homocysteinemia which has been observed in renal patients. Pyridoxine is a coenzyme for both cystathionine synthase and cystathionase, enzymes that catalyze the formation of cysteine from methionine. Homocysteine is an intermediate in this process and elevated levels of plasma homocysteine are recognized as a risk factor for vascular disease. Robinson et al., 94 CIRCULATION 2743–2748 (1996). However, it has been proposed that administration of pyridoxine may reduce the levels of homocysteine. Bostom et al., 49 KIDNEY INT. 147–152 (1996). Hence, one embodiment of the compositions of the present invention may comprise pyridoxine, preferably in the amount ranging from about 13.5 to about 16.5 mg.

Cyanocobalamin (vitamin $B_{12}$) is the pharmaceutical form of cobalamin which can be converted to the active coenzymes, methylcobalamin and 5'-deoxyadenosylcobalamin. These coenzymes are necessary for folic acid metabolism, conversion of coenzyme A, and myelin synthesis. For example, methylcobalamin catalyzes the demethylation of a folate cofactor which is involved in DNA synthesis. A lack of demethylation may result in folic acid deficiency. RDA, at 159–160. A deficiency of vitamin $B_{12}$ was observed in chronic renal failure patients and dialysis patients. In addition, slow nerve conduction velocities were also noted in dialysis patients. Rostand, 29 AM. J. CLIN. RES. 691–697 (1976). Based on these observations, vitamin $B_{12}$ supplementation may be appropriate as a means to compensate for any deficiency. Furthermore, since vitamin $B_{12}$ has a role in folic acid metabolism, supplementation may be effective in managing homocysteine levels in renal patients. Thus, the novel compositions of the present invention may comprise cyanocobalamin preferably in the amount ranging from about 10.8 to about 13.2 $\mu$g.

Biotin acts a coenzyme for a number of carboxylases and thus, has an important role in gluconeogenesis, fatty acid metabolism, and amino acid metabolism. RDA, at 166. It has been shown that biotin inhibits the effects of uremic toxins on tubulin polymerizaton. Braguer et al., 57 NEPHRON 192–196 (1991). Furthermore, there is some evidence to suggest that chronic renal failure patients and dialysis patients are at a risk for the development of a biotin deficiency. Mackenzie et al., 5 PROC. EUR. DIAL. TRANSPLANT. ASSOC. 172–178 (1968). In several dialysis patients diagnosed with uremic encephalopathy and neuropathy, symptoms of these disorders were alleviated by administration of biotin. Yatzidis et al., 305 N. ENGL. J. MED. 764 (1981). Thus, to maintain appropriate biotin levels in renal patients, one embodiment of the compositions of the present invention may comprise biotin preferably in an amount ranging from about 270 to about 330 $\mu$g.

Folic acid in its active form, tetrahydrofolate, is a coenzyme that is involved in the transfer of methyl groups and it plays a role in DNA synthesis, purine synthesis, and amino acid synthesis, such as the conversion of glycine to serine and the transformation of homocysteine to methionine. The activation of folic acid requires a vitamin $B_{12}$-dependent transmethylation and vitamin $B_{12}$ is also necessary for folic acid delivery to tissues. RDA, at 150. The metabolism of folic acid is altered by uremia and the absorption of tetrahydrofolate is impaired in chronic renal failure patients. Said et al., 6 ACTA VITAMINOL. ENZYMOL. 339–346 (1984). Furthermore, the diet generally prescribed for renal patients tends to be low in folic acid content and medications used by chronic renal failure patients may also inhibit the activity of folic acid. Stein et al., 3 BLOOD PURIF. 52–62 (1985); Cunningham et al., 282 BR. MED. J. 1582 (1981). The high incidence of homocysteinemia observed in chronic renal failure patients and the related risk of development of atherosclerosis suggest that folic acid supplementation may provide an effective method for managing this condition and also provide a cardio-protective effect. Robinson et al., 94 CIRCULATION 2743–2748 (1996). Therefore, in a preferred embodiment, the compositions of the present invention may comprise folic acid preferably in the amount ranging from about 2.25 to about 2.75 mg.

Diabetic nephropathy is a leading cause of end-stage renal disease with Type II diabetes comprising the largest disease group requiring renal support. Ibrahim et al., 13 BAILLIERES CLIN. ENDOCRINOL. METABOL. 239–264 (1999). The trace mineral, chromium, may promote insulin activity by increasing insulin binding and insulin receptor number. Chromium also activates the insulin receptor kinase leading to increased insulin sensitivity. Anderson et al., 26 DIABETES METABOL. 22–27 (2000). It is estimated that 90% of adults in the United States consume less than the recommended minimum amount of chromium. In addition, the typical renal diet is likely to be further restricted in chromium content. NUTRITION CONCEPTS AND CONTROVERSIES 293 (Sizer et al., $8^{th}$ ed.). Hence, to maintain appropriate chromium levels in renal patients, one embodiment of the compositions of the present invention may comprise chromium preferably in the amount ranging from about 180 to about 220 $\mu$g.

Selenium is a component of the antioxidant enzyme, glutathione peroxidase, which plays a critical role in the control of oxygen metabolism, particularly catalyzing the breakdown of hydrogen peroxide. Burk, 3 ANNU. REV. NUTR. 53–70 (1983). Glutathione peroxidase prevents the generation of free radicals and decreases the risk of oxidative damage to numerous tissues, including the vascular system. Holben, 99 J. AM. DIET. ASSOC. 836–843 (1999). Diabetic patients have even higher levels of oxidative stress due to the combination of diabetes and renal disease. Kedziora-Komatowska, et al., 11 NEPHROL. DIAL. TRANSPLANT. 2829–2832 (1998). Selenium may be lost during dialysis therapy and dietary selenium may be less than adequate due to protein restrictions. Several studies have demonstrated significant decreases in serum selenium, selenium-dependent enzymes, and increased lipid peroxidation in dialysis patients. Smith et al., 7 J. RENAL NUTR. 69–72 (1997); Zima et al., 16 BLOOD PURIF. 253–260 (1998). Oral and intravenous selenium supplementation has proven to be effective in improving the selenium status and immune function of renal patients, while decreasing the levels of oxidative stress products. Temple et al., 10 J. RENAL NUTR. 16 (2000). Therefore, in a preferred embodiment, the compositions of the present invention may comprise selenium preferably in amounts ranging from about 63 to about 77 μg.

There are more than 200 zinc metalloenzymes including aldolase, alcohol dehydrogenase, RNA polymerase, and protein kinase C. Thus, zinc plays a role in numerous metabolic activities such as nucleic acid production, protein synthesis, and development of the immune system. Zima et al., 17 BLOOD PURIF. 182–186 (1999). Several studies have shown decreased serum levels of zinc in dialysis patients and patients with renal failure. Thomson et al., 23 KIDNEY INT. 9–14 (1983); Muirhead et al., 6 AM. J. NEPHROL. 422–426 (1986). Zinc supplementation has been shown to improve a number of clinical symptoms observed in renal patients such as dygeusia, nerve conduction velocity, and impotency, and it has been proposed that zinc supplementation may restore impaired cell-mediated immunity and lymphocyte function. Zima et al., 17 BLOOD PURIF. 182–186 (1999). One embodiment of the compositions of the present invention provides a supplemental dose of zinc, preferably in the amount of about 18 to about 22 mg.

The compositions of the present invention are preferably administered in amounts to patients that provide the supplementation required to alleviate the vitamin and mineral deficiencies associated with renal disease. In a preferred embodiment of the present invention, the composition comprises 50 mg of vitamin C, 35 IU vitamin E, 3 mg of thiamine, 2 mg of riboflavin, 20 mg of niacin, 10 mg of pantothenic acid, 15 mg of pyridoxine, 12 μg cyanocobalamin, 300 μg of biotin, 2.5 mg of folic acid, 200 μg of chromium, 70 μg of selenium, and 20 mg of zinc.

In a further preferred embodiment, the composition comprises about 45 mg to 55 mg vitamin C, 31.5 IU to 38.5 IU vitamin E, 2.7 mg to 3.3 mg thiamine (vitamin $B_1$), 1.8 mg to 2.25 mg riboflavin (vitamin $B_2$), 18 mg to 22 mg niacin (vitamin $B_3$), 9 mg to 11 mg pantothenic acid (vitamin $B_5$), 13.5 mg to 16.5 mg pyridoxine (vitamin $B_6$), 10.8 μg to 13.2 μg cyanocobalamin (vitamin $B_{12}$), 270 μg to 330 μg biotin, 2.25 mg to 2.75 mg folic acid, 180 μg to 220 μg chromium, 63 μg to 77 μg selenium, and 18 mg to 22 mg zinc.

A preferred dosage of the compositions of the present invention may consist of one or more caplets for human oral consumption. If more than one caplet is used, each individual caplet may be identical to the other caplets, or each may contain only some of the ingredients of the composition, so that the combination of the different caplets comprises a composition of the present invention.

The compositions of the present invention represent a combination of essential vitamins and minerals that work together with various metabolic systems and physiological responses of the human body. The ingredients of the present invention are preferably combined into a composition which may be in the form of a solid powder, caplets, tablets, lozenges, pills, capsules, or a liquid, and which may be administered alone or in suitable combination with other components. For example, the composition of the present invention may be administered in one or more caplets or lozenges as practical for ease of administration. Each of the vitamins and minerals is commercially available, and can be blended to form a single composition or can form multiple compositions which may be co-administered.

To prepare the components of the present invention, each of the active ingredients may be combined in intimate admixture with a suitable carrier according to conventional compounding techniques. This carrier may take a wide variety of forms depending upon the form of the preparation desired for administration, e.g., oral, sublingual, nasal, topical patch, or parenteral. The composition may comprise one to three caplets or lozenges, the composition of each being identical to each other caplet or lozenge.

In preparing the composition in oral dosage form, any of the usual media may be utilized. For liquid preparations (e.g., suspensions, elixirs, and solutions) media containing for example water, oils, alcohols, flavoring agents, preservatives, coloring agents and the like may be used. Carriers such as starches, sugars, diluents, granulating agents, lubricants, binders, disintegrating agents and the like may be used to prepare oral solids (e.g., powders, caplets, pills, tablets, capsules, and lozenges). Controlled release forms may also be used. Because of their ease in administration, caplets, tablets, pills, and capsules represent the most advantageous oral dosage until form, in which case solid carriers are employed. If desired, tablets may be sugar coated or enteric coated by standard techniques.

The present invention also relates to methods for supplementing nutritional deficiencies in a patient. Specifically, the present invention relates to methods for supplementing the nutritional deficiencies in a patient comprising the step of administering to said patient compositions comprising vitamin C, vitamin E, B-complex vitamins, chromium, selenium, and zinc.

In a preferred embodiment of the present invention, the methods for supplementing nutritional deficiencies in a patient or person in need thereof, comprise the step of administering to said patient the composition comprising 50 mg of vitamin C, 35 IU vitamin E, 3 mg of thiamine, 2 mg of riboflavin, 20 mg of niacin, 10 mg of pantothenic acid, 15 mg of pyridoxine, 12 μg cyanocobalamin, 300 μg of biotin, 2.5 mg of folic acid, 200 μg of chromium, 70 μg of selenium, and 20 mg of zinc.

In a further preferred embodiment, the methods of the present invention comprise administering to a patient compositions comprising about 45 mg to 55 mg vitamin C, 31.5 IU to 38.5 IU vitamin E, 2.7 mg to 3.3 mg thiamine (vitamin $B_1$), 1.8 mg to 2.25 mg riboflavin (vitamin $B_2$), 18 mg to 22 mg niacin (vitamin $B_3$), 9 mg to 11 mg pantothenic acid (vitamin $B_5$), 13.5 mg to 16.5 mg pyridoxine (vitamin $B_6$), 10.8 μg to 13.2 μg cyanocobalamin (vitamin $B_{12}$), 270 μg to 330 μg biotin, 2.25 mg to 2.75 mg folic acid, 180 μg to 220 μg chromium, 63 μg to 77 μg selenium, and 18 mg to 22 mg zinc.

These methods also preferably compromise the administration of one or more of the compositions of the present invention to a patient afflicted with renal disease or renal insufficiency. In a preferred embodiment of the present invention, the methods preferably compromise the administration of one or more of the compositions to a patient suffering from end-stage renal disease and undergoing dialysis treatment. In a further preferred embodiment, the methods preferably comprise the administration of one or more of the compositions of the present invention to treat the nutritional deficiencies of any disease state that results in increased oxidative stress, elevated cholesterol levels, or elevated homocysteine levels.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description.

The invention will be further illustrated by the following non-limiting examples.

EXAMPLE 1

A composition of the following formulation was prepared in caplet form by standard methods known to those skilled in the art:

| | |
|---|---|
| Ascorbic acid | 50 mg |
| Biotin | 300 µg |
| Cyanocobalamin | 12 µg |
| d-Alpha Tocophenyl Succinate | 35 IU |
| d-Calcium Pantothenate | 10 mg |
| Folic acid | 2.5 mg |
| Niacinamide | 20 mg |
| Pyridoxine | 15 mg |
| Riboflavin | 2 mg |
| Thiamine | 3 mg |
| Chromium Chloride | 200 µg |
| L-Selenomethionine | 70 µg |
| L-Optizinc ZML-200 Inter-Health (zinc L-methionine) | 20 mg |

One (1) caplet per day is the recommended dosage or as recommended by physician.

EXAMPLE 2

A study is undertaken to evaluate the effectiveness of the composition of the present invention in the treatment of patients diagnosed with end-stage renal disease (ESRD). The objective of the study is to determine whether oral intake of the composition results in an improvement of the nutritional status of the patient.

A double-blind, placebo controlled study is conducted over a twelve-month period. A total of sixty subjects (30 men and 30 women) aged 40 to 85 years, suffering from ESRD, are chosen for the study. An initial assessment of nutritional status is conducted utilizing methods such as the peroxide hemolysis test to assess vitamin E deficiency, measurement of erythrocyte transketolase activity to determine thiamine levels, determination of erythrocyte glutathione reductase activity to assess riboflavin status, and high performance liquid chromatography to directly measure PLP and pyridoxine levels.

The sixty subjects are separated into two separate groups of fifteen men and fifteen women. In the first group, each subject is administered 1 to 2 caplets, daily, of the composition as described in example 1. In the second group (control) each subject is administered 1 to 2 placebo caplets, daily.

An assessment of nutritional status for each subject is measured at one-month intervals for a twelve month period as described above and the data is evaluated using multiple linear regression analysis and a standard students t-test. In each analysis the baseline value of the outcome variable is included in the model as a covariant. Treatment by covariant interaction effects is tested by the method outlined by Weigel & Narvaez, 12 CONTROLLED CLINICAL TRALS 378–94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 18, 12, and 6 weeks, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

A statistically significant improvement in the nutritional status is observed in the treated subjects upon completion of the study but not the controls. The differences between nutritional state in the treated subjects and controls are statistically significant. Therefore, the study confirms that oral administration of the composition of the present invention is effective in the treatment of patients diagnosed with ESRD.

We claim:

1. A composition comprising:
about 63 µg to about 77 µg selenium; about 18 mg to about 22 mg zinc; about 45 mg to about 55 mg of vitamin C; about 31.5 IU to about 38.5 IU vitamin E; about 2.25 mg to about 2.75 mg folic acid; about 270 µg to about 330 µg biotin; about 9 mg to about 11 mg pantothenic acid; about 18 mg to about 22 mg niacin; about 13.5 mg to about 16.5 mg pyridoxine; about 1.8 mg to about 2.25 mg riboflavin; about 10.8 µg to about 13.2 µg cyanocobalamin; and about 2.7 mg to about 3.3 mg thiamine, wherein said composition is free of added chromium any other added minerals and any other added vitamins.

2. The composition of claim 1, wherein said selenium comprises L-selenomethionine.

3. The composition of claim 1, wherein said zinc comprises zinc L-methionine.

4. The composition of claim 1, wherein said vitamin C comprises ascorbic acid.

5. The composition of claim 1, wherein said vitamin E comprises d-alpha tocopheryl succinate.

6. The composition of claim 1, wherein said pantothenic acid comprises d-calcium pantothenate.

7. The composition of claim 1, wherein said niacin comprises niacinamide.

8. The composition of claim 1, wherein said composition further comprises a pharmaceutically acceptable carrier.

9. A method for supplementing nutritional deficiencies in a patient or person in need thereof, comprising the step of administering to said patient the composition of claim 1.

10. The method of claim 9, wherein said composition further comprises pharmaceutically acceptable carrier.

11. The method of claim 9, wherein said patient is suffering from kidney disease.

12. The method of claim 11, wherein said kidney disease is end-stage renal disease.

13. The method of claim 9, wherein said patient is suffering from renal insufficiency.

14. The method of claim 9, wherein said patient is undergoing dialysis therapy.

15. The composition of claim 9, wherein said nutritional deficiencies are a result of dietary restrictions.

16. The composition of claim 9, wherein said nutritional deficiencies are a result of a disease state.

17. The composition of claim 16, wherein said disease state is kidney disease.

18. The composition of claim 17, wherein said kidney disease is end-stage renal disease.

19. The composition of claim 9, wherein said nutritional deficiencies are a result of dialysis therapy.

20. The composition of claim 9, wherein said disease state leads to increased oxidative stress in said patient.

21. The composition of claim 9, wherein said disease state leads to elevated cholesterol levels in said patient.

22. A method for supplementing nutritional deficiencies in a patient suffering from kidney disease comprising the step of administering to said patient the composition of claim 1.

23. The method of claim 22, wherein said composition further comprises pharmaceutically acceptable carrier.

24. The method of claim 22, wherein said composition is administered to said patient daily.

25. The method of claim 22, wherein said composition is administered to said patient orally.

26. A method for supplementing nutritional deficiencies in a patient suffering from end-stage renal disease comprising the step of administering to said patient the composition of claim 1.

27. The method of claim 26, wherein said composition further comprises a pharmaceutically acceptable carrier.

28. The method of claim 26, wherein said composition is administered to said patient daily.

29. The method of claim 26, wherein said composition is administered to said patient orally.

30. A method for supplementing nutritional deficiencies in a patient suffering undergoing dialysis therapy comprising the step of administering to said patient the composition of claim 1.

31. The method of claim 30, wherein said composition further comprises pharmaceutically acceptable carrier.

32. The method of claim 30, wherein said composition is administered to said patient daily.

33. The method of claim 30, wherein said composition is administered to said patient orally.

* * * * *

UNITED STATES PATENT AND TRADEMARK OFFICE
CERTIFICATE OF CORRECTION

PATENT NO.        : 6,995,166 B1
APPLICATION NO. : 09/671283
DATED             : February 7, 2006
INVENTOR(S)      : John A. Giordano et al.

It is certified that error appears in the above-identified patent and that said Letters Patent is hereby corrected as shown below:

Column 10, Claim 1, line 51-52, delete "added chromium";

Column 12, Claim 30, line 19, delete "suffering";

Claim 31, line 23, insert after comprises --a--.

Signed and Sealed this

Thirty-first Day of October, 2006

JON W. DUDAS
*Director of the United States Patent and Trademark Office*